United States Patent [19]

Kobayashi et al.

[11] 4,229,600
[45] Oct. 21, 1980

[54] NORBORNANE AND NORBORNENE DERIVATIVES

[75] Inventors: Toyohiko Kobayashi; Haruki Tsuruta; Toshio Yoshida, all of Yokohama, Japan

[73] Assignee: Takasago Perfumery Co., Ltd., Tokyo, Japan

[21] Appl. No.: 929,055

[22] Filed: Jul. 28, 1978

[30] Foreign Application Priority Data

Jul. 28, 1977 [JP] Japan ............................ 52/90846
Nov. 14, 1977 [JP] Japan ........................... 52/136547

[51] Int. Cl.³ ...................... C07C 31/13; C07C 33/05
[52] U.S. Cl. .................................. 568/820; 252/522 R
[58] Field of Search ............ 568/820; 260/598, 586 C

[56] References Cited

U.S. PATENT DOCUMENTS

| | | | |
|---|---|---|---|
| 2,373,568 | 4/1945 | Joy et al. ............................ | 260/598 |
| 3,067,244 | 12/1962 | Robinson et al. ..................... | 260/598 |
| 3,914,322 | 10/1975 | Chappell et al. ..................... | 568/820 |
| 3,942,761 | 3/1976 | Schleppni ........................... | 260/586 C |
| 4,076,853 | 2/1978 | Light et al. ........................ | 568/820 |
| 4,128,509 | 12/1978 | Schleppni ........................... | 568/820 |

FOREIGN PATENT DOCUMENTS 623999 7/1961 Canada .................................... 568/820

Primary Examiner—Norman Morgenstern
Attorney, Agent, or Firm—Sughrue, Rothwell, Mion, Zinn and Macpeak

[57] ABSTRACT

A norbornane or norbornene derivative of the formula (I):

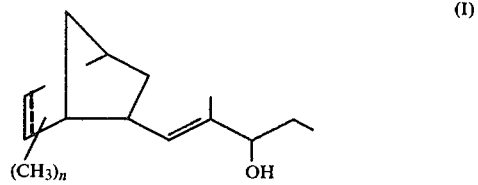

wherein the bond represented by the dotted line is present or absent and n is 0 or 1, the norbornane and norbornene derivatives having a characteristic odor of sandalwood oil and useful for perfumery; and a process for the production thereof.

3 Claims, 4 Drawing Figures

FIG. I

NORBORNANE AND NORBORNENE DERIVATIVES

BACKGROUND OF THE INVENTION

1. Field of the Invention

This invention relates to a novel norbornane or norbornene derivative expressed by the following formula (I):

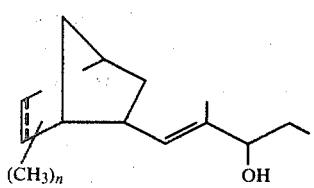

wherein the bond shown by the dotted line is present or absent and n is 0 or 1.

2. Description of the Prior Art

Natural sandalwood oil is obtained by the steam distillation of the heartwood and roots of sandalwood occurring in India and Malasia, and is an important ingredient of mixed perfumes of an Oriental note. Sandalwood is a special plant which lives upon the roots of other trees by stretching long suckers from its roots. It is cultivated from seeds, and a period of as long as 30 years is required until sandalwood oil can be extracted from it. Accordingly, resources have become scarce in India which is a main country producing sandalwood oil, and the supply of sandalwood oil has become short in recent years. This has caused an increase in the cost of sandalwood oil. The principal ingredient of natural sandalwood oil is a mixture of α-santalol and β-santalol (hereinafter α,β-santalol) of the structures

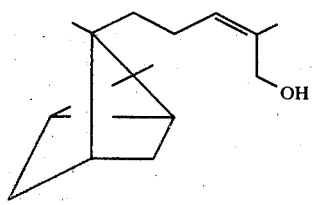

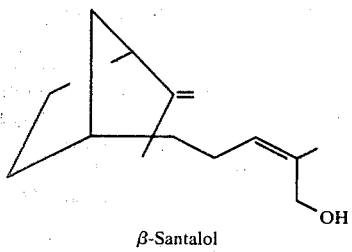

and the commercial production of α,β-santalol has not been successfully achieved. Naturally, development of a synthetic perfume having an odor similar to α,β-santalol has been desired, and several products which are similar in odor to but quite distinct in structure from sandalwood oil have been offered on the market. However, none of them meet the needs of the consumers from the standpoint of cost and odor.

SUMMARY OF THE INVENTION

Extensive investigations have now been made in an attempt to meet such a need, and as a result the synthesis of novel compounds of formula (I) below, having odors similar to α,β-santalol, has been accomplished.

Accordingly, an object of this invention is to provide compounds having odors similar to α,β-santalol.

Another object of this invention is to provide a process for producing compounds having odors similar to α,β-santalol.

This invention thus in one embodiment provides a norbornane or norbornene derivative of the formula (I):

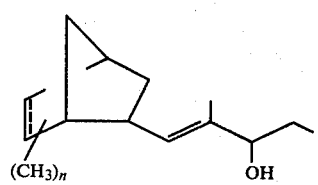

wherein the bond represented by the dotted line is present or absent and n is 0 or 1.

BRIEF DESCRIPTION OF THE ACCOMPANYING DRAWINGS

DETAILED DESCRIPTION OF THE INVENTION

Figure 1:
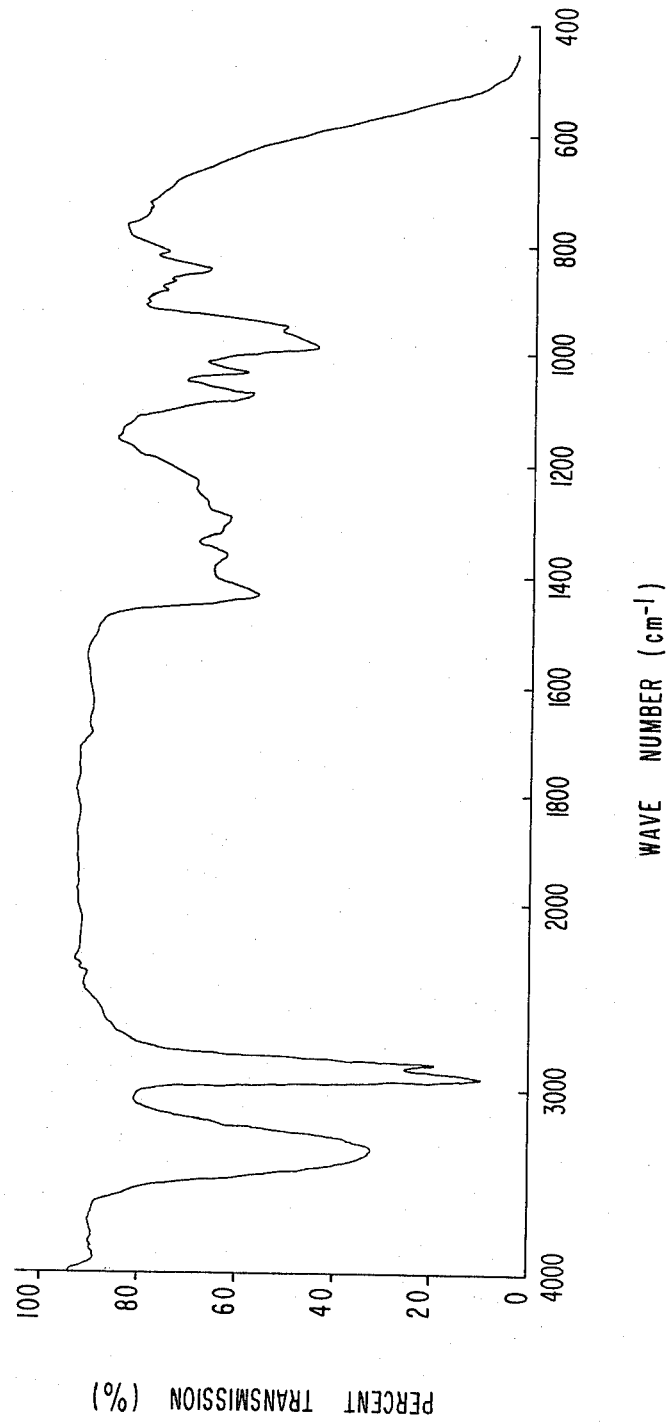
FIG. 1 shows the infrared absorption spectrum of the norbornane derivative of the formula $(I-B_0)$.
Figure 2:
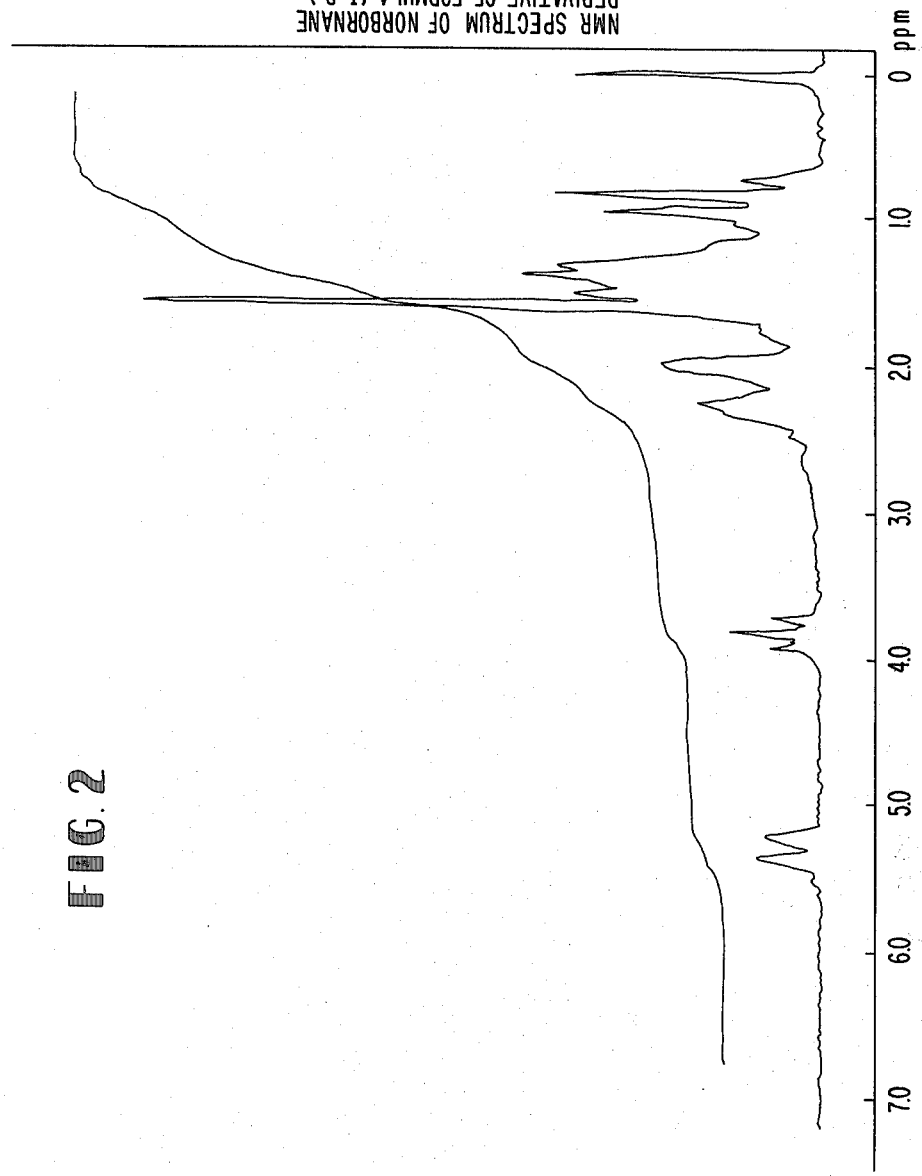
FIG. 2 shows the NMR spectrum of the norbornane derivative of the formula $(I-B_0)$.
Figure 3:
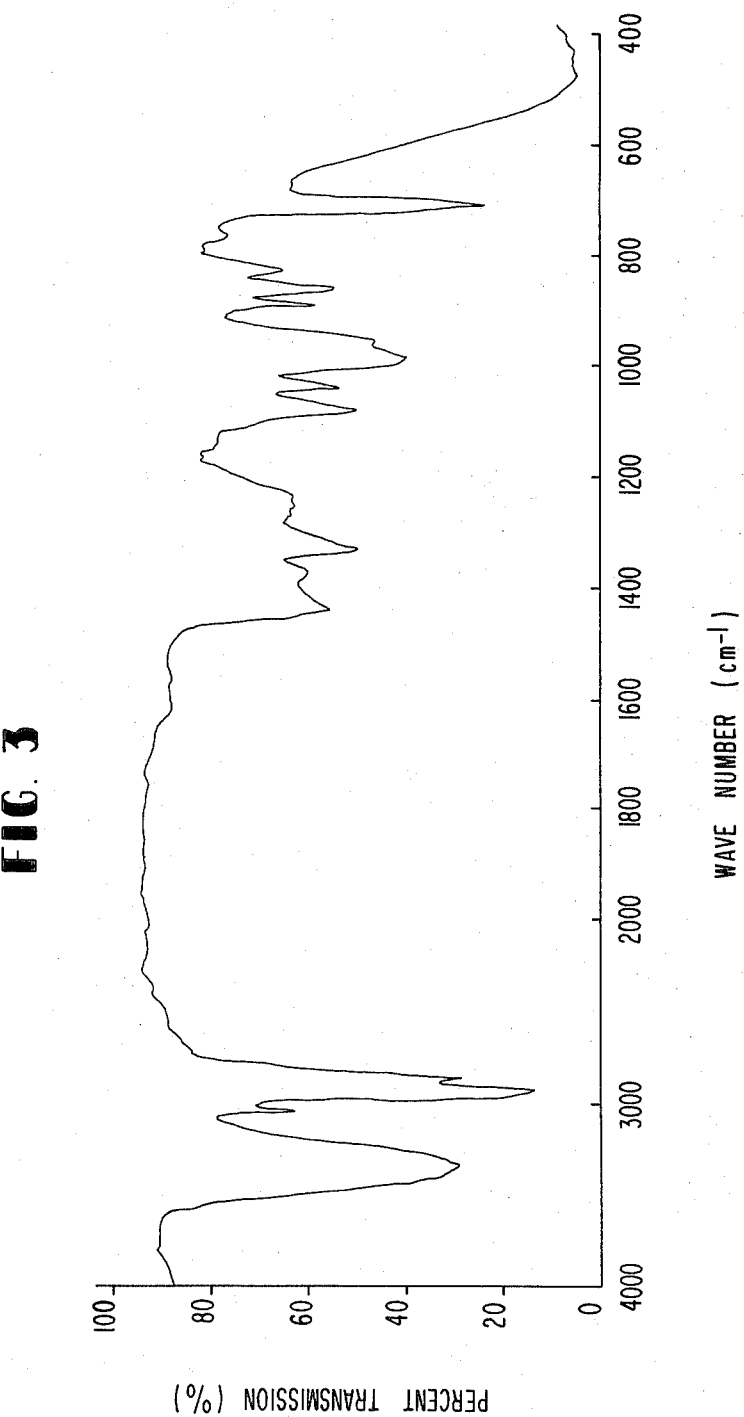
FIG. 3 shows the infrared absorption spectrum of the norbornene derivative of the formula $(I-A_0)$.
Figure 4:
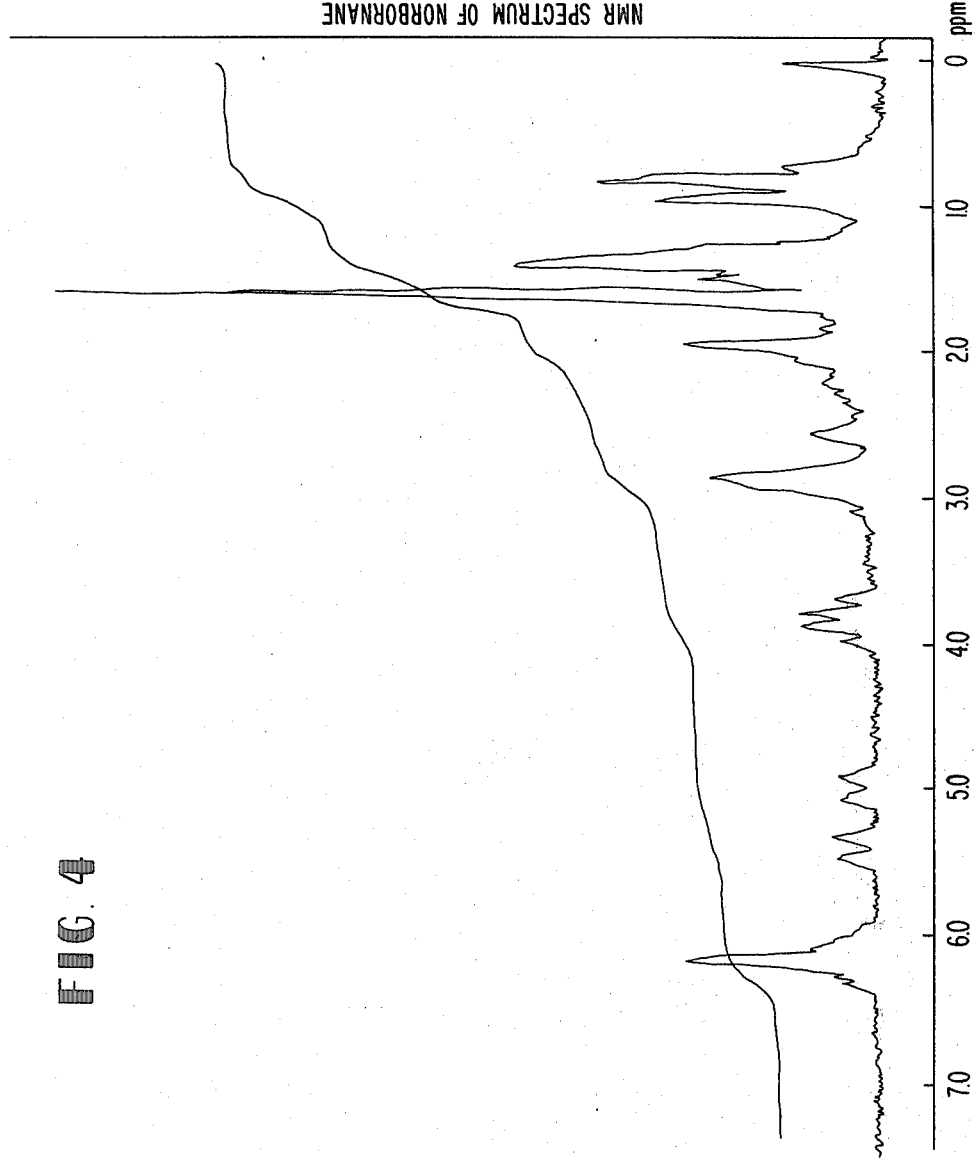
FIG. 4 shows the NMR spectrum of the norbornene derivative of the formula $(I-A_0)$.

The compound (I) of this invention has a sandalwood odor. In particular, the norbornene derivatives [compounds of the formula (I) in which the bond represented by the dotted line is present and n is either 0 or 1] have a strong sandalwood odor, and the norbornane derivatives [compounds of the formula (I) in which the bond represented by the dotted line is absent and n is either 0 or 1] have a sandalwood odor with a green note. All of these compounds are important as perfumes and as components in perfume compositions.

The compound (I) of the invention can be prepared in accordance with the following reaction scheme (A).

REACTION SCHEME (A)

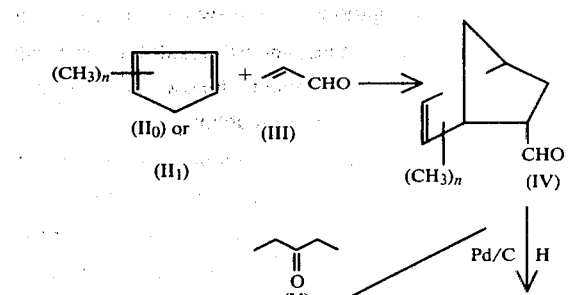

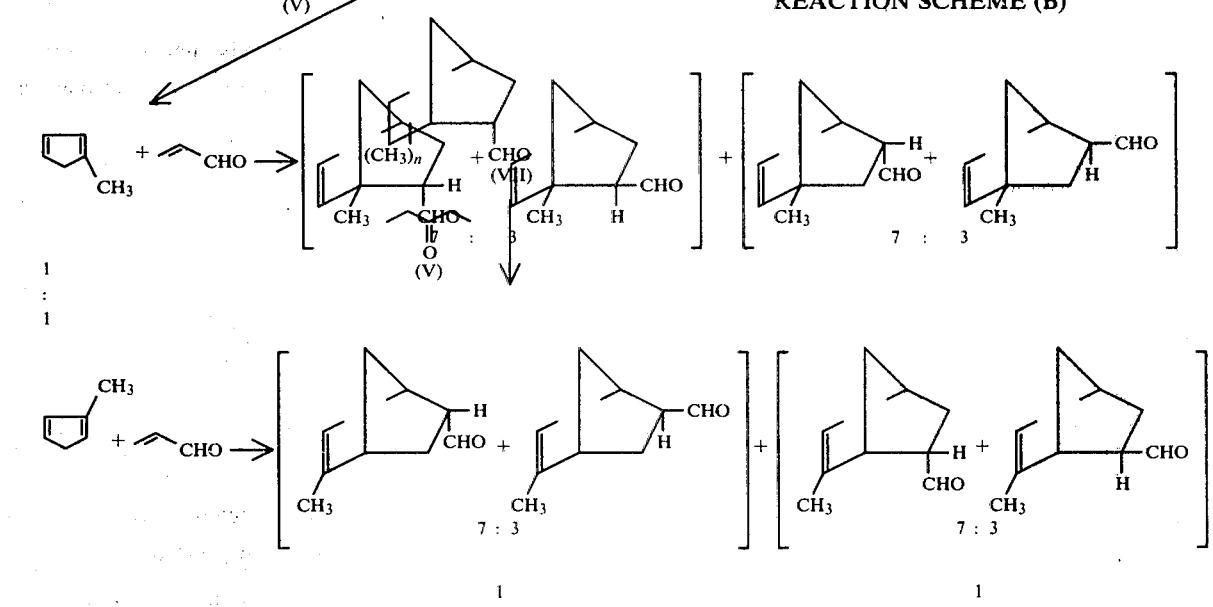

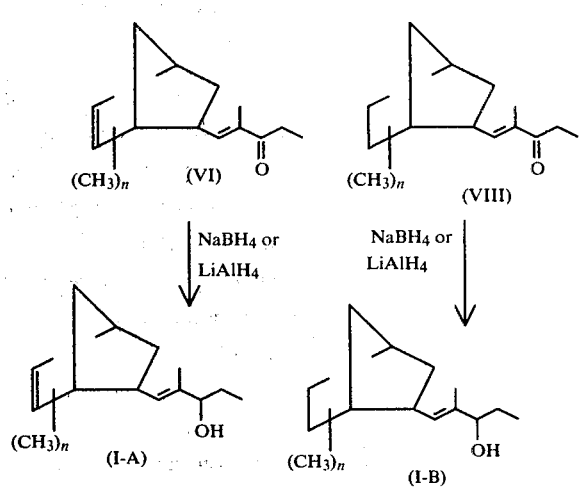

In the description given herein, the subscript "0" is used with the Roman numeral formula designations to indicate that "n is 0" and the suscript "1" is used with the Roman numeral formula designations to indicate that "n is 1". Where no such subscript is present, n can be either 0 or 1.

Specifically, the norbornene derivative of formula (I-A) can be obtained as follows. Cyclcopentadiene (II$_0$) where n is 0 or methylcyclopentadiene (II$_1$) where n is 1 and acrolein (III) are subjected to a Diels-Alder reaction to form an adduct (IV). The adduct (IV$_1$) where n is 1 in the formula of adduct (IV) comprises eight isomers as illustrated in reaction scheme (B) below.

REACTION SCHEME (B)

These isomers are difficult to separate, but the isomers can be used in the form of a mixture thereof without difficulty for the purpose of a perfume. This type of adduct will hereinafter be referred to simply as adduct (IV). The Diels-Alder reaction which can be employed in this invention in the reaction of cyclopentadiene (II$_0$) or methylcyclopentadiene (II$_1$) and the acrolein (III) can be carried out using reaction conditions as described in R. Adams, *Organic Reactions*, vol. IV, May, 1949, pp 89-90. The Diels-Alder reaction can be suitably carried out at room temperature (e.g., about 20°-30° C.) using equimolar amounts of the starting compounds of the formulae (II) and (III). Since the Diels-Alder reaction proceeds as an exothermic reaction through simply mixing the starting compounds (II) and (III), the reaction system must be cooled to room temperature. An inert solvent is used for the Diels-Alder reaction, and examples of suitable solvents which can be used are benzene, toluene, diethyl ether, tetrahydrofuran, etc.

The adduct (IV) obtained in this step is then condensed with diethyl ketone (V) in the presence of an alkali to form a ketone compound (VI). The condensation of the adduct (IV) with the diethyl ketone (V) can be carried out for about 2 to about 3 hours under reflux conditions under heating e.g., in methanol, in the presence of an alkali such as sodium hydroxide, potassium hydroxide, etc. A suitable amount of diethyl ketone (V) which can be used is an amount of about 2.5 to about 3 times the equivalent amount to the adduct (IV). A suitable amount of the alkali which can be used is about one-fourth of the weight of the adduct (IV) used. A 0.3 N methanol solution of an alkali is preferred. The methanol can be recovered from the reaction solution after the reaction is completed under reduced pressure, and the resulting concentrate is dissolved in an ether such as diethyl ether. The resulting mixture is then washed e.g., three times with a saturated aqueous solution of sodium chloride, and the ether is then evaporated off. The residue is distilled to obtain the ketone compound (VI). The ketone compound (VI) obtained includes both cis- and trans-isomers of the side chain double bonds in the molecule thereof. These isomers are difficult to separate. However, isomers of the ketone compound (VI) can be used in the form of a mixture thereof without difficulty for the purpose of a perfume. The thus obtained ketone compound (VI) is then reduced with sodium borohydride or with lithium aluminum hydride to obtain the compound (I-A).

Where the ketone compound (VI) is reduced with sodium borohydride, the reaction in which a 1.5 equivalent (corresponding to 0.38 mole) amount of sodium borohydride to that of the starting ketone compound (VI) is preferably carried out in an aqueous methanol solution. In this case, in order to prevent sodium borohydride from decomposing, an alkali is added to the reaction system. A sufficient amount of alkali which can be used is about 10 to about 15% by weight based on the amount of sodium borohydride present. The amount of methanol which can be used is at least about 1.5 to about 2 times by weight to the weight of the starting compound (VI), with a larger amount of methanol being preferred. Water is added so as to prepare an approximately 75% aqueous methanol solution. The reduction reaction can be carried out at a temperature of about 40° C. for about 1.5 to about 2 hours. The methanol is removed under reduced pressure from the reaction solution, and the residue is dissolved in e.g., toluene, and the resulting mixture is washed with a saturated aqueous solution of sodium chloride. The toluene is then evaporated off, and the residue is distilled to obtain the desired compound (I-A).

On the other hand, where the reduction of the ketone compound (VI) is carried out using lithium aluminum hydride, the reduction can be performed in anhydrous diethyl ether at a temperature of about 5 to about 10° C. e.g., with ice cooling. A suitable amount of lithium aluminum hydride is about 1.5 equivalent (corresponding to 0.38 mole) amount to that of the starting ketone compound (VI), and a suitable amount of the diethyl ether is about 10 times by weight to the weight of the starting ketone compound (VI). After the reduction reaction, water is added to the reaction solution to decompose the remaining lithium aluminum hydride, and the ethereal layer is dried over e.g., anhydrous sodium sulfate. Thereafter, the diethyl ether is evaporated off to obtain the desired compound (I-A) by distillation under reduced pressure.

The norbornane derivative of the formula (I-B) can be obtained as follows. Cyclopentadiene ($II_0$) or methylcyclopentadiene ($II_1$) and acrolein (III) are reacted in a Diels-Alder reaction to produce an adduct (IV) as described above. Then, the adduct (IV) is catalytically reduced in the presence of a palladium catalyst, etc. to form a compound of the formula (VII).

The catalytic reduction of the adduct (IV) in the presence of a palladium catalyst to produce the compound (VII) can be carried out in, e.g., cyclohexane in the presence of a palladium catalyst (e.g., a palladium-on-carbon catalyst containing 5% by weight of palladium) in an amount of about 1% by weight based on the amount of the starting adduct (IV) under a hydrogen pressure of about 5 to about 10 Kg/cm$^2$ until the theoretical amount of hydrogen has been absorbed. The reaction solution is filtered to remove the catalyst, the cyclohexane is evaporated off, and the residue is distilled under reduced pressure to obtain the compound (VII).

The compound of the formula (VII) is then reacted with diethyl ketone (V) in the presence of an alkali in the same manner as described above for the reaction of the adduct (IV) and the diethyl ketone (V), to obtain the ketone compound (VIII). The ketone compound (VIII) is then reduced with sodium borohydride or lithium aluminum hydride, as described above in the reduction of the ketone compound (VI), to obtain the compound of the formula (I-B).

Cyclopentadiene is used as a starting material in this invention to produce the compounds of the formula (I) where n is 0 and methylcyclopentadiene is used as a starting material in this invention to produce the compounds of the formula (I) where n is 1. Methylcyclopentadiene is an unstable compound, and is sold on the market as a dimer. Heating the dimer to 180° C. results in the formation of a mixture containing a 2-methyl isomer and a 3-methyl isomer in a molar ratio of 1:1. These isomers are difficult to separate even by distillation or the like. However, the object of this invention in producing compounds of the formula (I) where n is 1 can be achieved by using this isomer mixture. This 1:1 mixture of the 2-methyl isomer and the 3-methyl isomer is referred to herein simply as methylcyclopentadiene.

The following Formulation Examples are given to illustrate representative examples of perfumes in which the compounds of the formula (I) of this invention can be used. These Formulation Examples should not be construed as limiting the use of the compounds of the formula (I) of this invention, however.

FORMULATION EXAMPLE 1

The following components were mixed in the amounts shown to produce a perfume for soaps having an Oriental-type perfume with graceful top notes and a strong odor retentivity.

| Components | parts by weight |
|---|---|
| Compound (I-A*) of the Invention | 150 |
| Cedrol | 100 |
| Ethylene Brassylate | 120 |
| Musk Ketone | 30 |
| Benzyl Salicylate | 60 |
| Isoamyl Salicylate | 40 |
| Methyl Ionone | 70 |
| p-t-Butyl Cyclohexyl Acetate | 150 |
| Dimethyl Benzyl Carbinyl Acetate | 20 |
| α-Hexyl Cinnamic Aldehyde | 50 |
| Indole (10%) | 20 |
| Benzyl Acetate | 50 |
| Styralyl Acetate | 40 |
| Aldehyde $C_{10}$ | 2 |
| Aldehyde $C_{11}$ | 3 |
| 9-Decenol-1 | 5 |
| Lavandine Oil | 90 |
| Total | 1000 |

*Compound (I-A$_0$) or (I-A$_1$) can be used.

FORMULATION EXAMPLE 2

The following components were mixed in the amounts indicated to produce a woody-type perfume useful as a perfume or as an eau-de-Cologne.

| Components | parts by weight |
|---|---|
| Compound (I-B*) of the Invention | 220 |
| Sandalwood Oil | 70 |
| Vaniline | 3 |
| Ethyl Vaniline | 2 |
| Labdanum Absolute | 20 |
| Vertofix (a product of International Flavors and Fragrances Co.) | 100 |
| Oak Moss Absolute | 30 |
| Isobutyl Quinoline (10%) | 20 |
| γ-Methyl Ionone | 50 |
| Hydroxyl Citronellal | 60 |
| α-Hexyl Cinnamic Aldehyde | 90 |
| Jasmine Base | 50 |
| Benzyl Acetate | 40 |
| Ylang Ylang Oil | 40 |
| Phenylethyl Alcohol | 50 |
| Rose Base | 70 |
| Aldehyde $C_{11}$ (10%) | 20 |
| Galvanum Oil | 5 |
| Bergamot Oil | 60 |
| Total | 1000 |

*Compound (I-B$_0$) or (I-B$_1$) can be used.

The following Examples are given to illustrate the present invention in greater detail. In the description to follow, the subscript "0" and the subscript "1" will be used to indicate that n is 0 and n is 1, respectively. Further, unless otherwise indicated, all parts, percents, ratios, and the like are by weight.

EXAMPLE 1

(i) Cyclopentadiene (460 g) was placed in a 3-liter flask, and with stirring under ice cooling (at 5°–10° C.), a mixture of 433 g of acrolein and 500 ml of diethyl ether was added dropwise thereto over the course of 2 hours while maintaining the temperature of the inside of the flask at 25° to 30° C. The reaction was continued at this temperature for 15 hours. After the reaction, the contents of the flask were transferred to a distillation flask, and the diethyl ether was distilled off. Distillation under reduced pressure afforded 728.1 g of a fraction having a boiling point of 70°–72° C./19 mmHg. From the IR spectrum of this fraction (1710 cm$^{-1}$ and 715 cm$^{-1}$), the product was identified as compound (IV$_0$).

(ii) A 3-liter reaction flask was charged with 1.5 liters of methanol, 50 g of a 40% aqueous solution of sodium hydroxide and 456 g of diethyl ketone, and on heating the reaction mixture under reflux, 244 g of compound (IV$_0$) was added dropwise thereto at 62° C. over the course of 45 minutes. The mixture was heated under reflux for two additional hours. Methanol was distilled off under reduced pressure, and 500 ml of diethyl ether was added to the concentrate. The solution was washed three times with 300 ml of a saturated aqueous solution of sodium chloride. The diethyl ether solution was placed in a distillation flask, and the diethyl ether was distilled off. Subsequent distillation under reduced pressure afforded 313.5 g of a fraction having a boiling point of 82°–87° C./1.5 mmHg. The product was identified as compound (VI$_0$) from the following data.

IR (1660 cm$^{-1}$, 710 cm$^{-1}$); NMR [6.0—6.8 (m, 3H), 1.8 (bs, 3H), 1.05 (t, 3H)].

(iii) A 1-liter reaction flask was charged with 190 g of compound (VI$_0$), 224 ml of methanol and 8 g of a 15% aqueous solution of potassium hydroxide, and while stirring the mixture at 40° C., a solution of 14.2 g of sodium borohydride, 0.88 g of potassium hydroxide, 112 ml of water and 112 ml of methanol was added dropwise thereto over the course of 1 hour. The mixture was further stirred for 30 minutes. After the reaction, methanol was distilled off under reduced pressure. To the resulting concentrate was added 300 ml of toluene. The toluene solution was washed twice with 300 ml of a saturated aqueous solution of sodium chloride. The toluene solution was transferred to a distillation flask, and under reduced pressure, the toluene was distilled off. The residual solution was distilled under reduced pressure to afford 154.8 g of a fraction having a boiling point of 89°–95° C./1.5 mmHg.

The product was identified as compound (I-A$_0$) from the following data.

IR (3350 cm$^{-1}$, 710 cm$^{-1}$); NMR [6.15 (b, 2H); 5.37, 4.95 (bd, 1H); 3.80 (q, 1H); 1.60 (bs, 3H); 0.80 (t, 3H)].

EXAMPLE 2

(i) A 200 ml autoclave was charged with 24.4 g of compound (IV$_0$) obtained as described in Example 1, 24 ml of cyclohexane and 0.24 g of a 5% palladium-on-activated carbon catalyst, and under ice cooling (at 5°–10° C.), hydrogen was introduced into the autoclave under a hydrogen pressure of 5 to 10 kg/cm$^2$. The reaction was stopped when the theoretical amount of hydrogen had been absorbed. The reaction solution was filtered to remove the catalyst, and the cyclohexane was distilled off under reduced pressure. 25.9 g of a residue was obtained. In gas-chromatographic analysis, this residue gave a single peak, and was identified as compound (VII$_0$).

(ii) A 300 ml. reaction flask was charged with 5 g of a 40% aqueous solution of sodium hydroxide, 150 ml of methanol, and 46 g of diethyl ketone, and while heating the mixture under reflux, 25.9 of compound (VII$_0$) was added dropwise thereto over the course of 15 minutes. The mixture was heated at reflux for 2 additional hours. The methanol was distilled off under reduced pressure, and 100 ml of diethyl ether was added to the concentrate. The solution was then washed three times with 100 ml of a saturated aqueous solution of sodium chloride, and transferred to a distillation flask. The diethyl ether was distilled off, and the residue was distilled under reduced pressure to afford 27.5 g of compound (VIII$_0$) having a boiling point of 87° to 93° C./1.5 mmHg.

IR: 1660 cm$^{-1}$

NMR: 6.47 (bd, 9.0 Hz, 1H)

(iii) 13 g of compound (VIII$_0$) obtained in (ii) above was placed in a 200 ml. reaction flask, and 130 ml of diethyl ether was added thereto. With stirring under ice cooling (at 5°–10° C.), 1.5 g of lithium aluminum hydride was added in small portions, and the reaction was further continued for 1.5 hours. 100 ml of water was added to the reaction solution, and the mixture was stirred. The ethereal layer was fractionated and dried over anhydrous sodium sulfate, and then the diethyl ether was distilled off. The residue was distilled under reduced pressure to afford 9.0 g of a fraction having a boiling point of 92°–95° C./1.5 mmHg. The product was identified as the compound of the formula (I-B$_0$) from the following data.

IR: (3340 cm$^{-1}$)

NMR: [5.28 (bd, 9.0 Hz, 1H), 3.80 (t, 6 Hz, 1H), 0.82 (t, 9.5 Hz, 3H)].

EXAMPLE 3

(i) Methylcyclopentadiene (400 g) and 1 g of hydroquinone (as a stabilizer) were placed in a 3-liter reaction flask, and with stirring under ice cooling (at 5°–10° C.), a mixture of 311 g of acrolein and 440 ml of tetrahydrofuran was added dropwise thereto over the course of 2 hours while maintaining the temperature of the contents of the flask at 25° to 30° C. The reaction was continued at this temperature for 15 hours. After the reaction, the contents were transferred to a distillation flask, and the tetrahydrofuran was distilled off. The residue was distilled under reduced pressure to afford 658.1 g of a fraction having a boiling point of 70° to 72° C./15 mmHg. This fraction was identified as the compound of formula (IV$_1$) from the AR spectrum thereof (1710 cm$^{-1}$, 715 cm$^{-1}$)b (ii) A 3-liter reaction flask was charged with 1.2 liters of methanol, 50 g of a 40% aqueous solution of sodium hydroxide, and 430 g of diethyl ketone, and while heating the mixture under reflux, 340 g of the compound (IV$_1$) was added dropwise thereto over the course of 45 minutes at 62° C. The mixture was further heated under reflux for 2 hours. Under reduced pressure, the methanol was distilled off. To the concentrate was added 500 ml of diethyl ether, and the mixture was washed three times with 300 ml of a saturated aqueous solution of sodium chloride. The ether solution was placed in a distillation flask, and the diethyl ether was distilled off. The residue was distilled under reduced pressure to afford 233 g of a fraction having a boiling point of 91° to 93° C./20 mmHg. This fraction was identified as the compound (VI$_1$) from the IR spectrum thereof (1660 cm$^{-1}$, 710 cm$^{-1}$).

(iii) A 1-liter reaction flask was charged with 204 g of the compound (VI$_1$), 224 ml of methanol, and 8 g of a 15% aqueous solution of potassium hydroxide, and with stirring at 40° C., a solution of 14.2 g of sodium borohydride, 0.88 g of potassium hydroxide, 112 ml of water and 112 ml of methanol was added dropwise thereto over the course of one hour. The mixture was stirred further for 30 minutes. After the reaction, the methanol was distilled off under reduced pressure. To the concentrate was added 300 ml of toluene. The toluene solution was wshed two times with 300 ml of a saturated aqueous solution of sodium chloride. The toluene solution was transferred to a distillation flask, and the toluene was distilled off under reduced pressure. The residue was distilled under reduced pressure to afford 143 g of a fraction having a boiling point of 80° to 81° C./1.0 mmHg. This fraction was identified as the compound of formula (I-A$_1$) from the IR spectrum (3350 cm$^{-1}$, 710 cm$^{-1}$).

EXAMPLE 4

(i) A 200 ml. autoclave was charged with 27.2 g of the compound (IV$_1$) obtained as described in Example 3, 27 ml of cyclohexane and 0.27 g of a 5% palladium-on-activated carbon catalyst. Under ice cooling (at 5°–10° C.), hydrogen was introduced at a hydrogen pressure of 5 to 10 kg/cm$^2$. The reaction was stopped on absorption of a theoretical amount of hydrogen. The reaction solution was filtered to remove the catalyst, and the cyclohexane was distilled off under reduced pressure to afford 27.9 g of a residue. This residue was identified as the compound of the formula (VII$_1$) by gas-chromatographic analysis.

(ii) a 300 m. reaction flask was charged with 5 g of a 40% aqueous solution of sodium hydroxide, 150 ml of methanol and 46 g of diethyl ketone. On heating under reflux, 27.9 g of the compound (VII$_1$) was added dropwise thereto over the course of 15 minutes. The mixture was further heated under reflux for 2 hours. The methanol was distilled off under reduced pressure, and 100 ml of diethyl ether was added to the concentrate. The ethereal solution was washed three times with 100 ml of a saturated aqueous solution of sodium chloride, and transferred to a distillation flask. The ether was distilled off. The residue was distilled under reduced pressure to afford 27.5 g of compound (VIII$_1$) having a boiling point of 85° to 91° C./1.7 mmHg.

IR: 1660 cm$^{-1}$.

(iii) 13 g of compound (VIII$_1$) obtained above was placed in a 200 ml reaction flask, and 130 ml of diethyl ether was added thereto. With stirring under ice cooling (at 5°–10° C.), 1.5 g of lithium aluminum hydride was added in small portions thereto. The reaction was performed for 1.5 hours. 100 ml of water was added to the reaction mixture, and the mixture was stirred to achieve decomposition. The ethereal layer was fractionated, and dried over anhydrous sodium sulfate. The diethyl ether was distilled off. The residue was distilled under reduced pressure to afford 9.0 g of a fraction having a boiling point of 86° to 91° C./1.0 mmHg. This fraction was identified as the compound of formula (I-B$_1$) from the IR spectrum thereof (3340 cm$^{-1}$).

While the invention has been described in detail and with reference to specific embodiments thereof, it will be apparent to one skilled in the art that various changes and modifications can be made therein without departing from the spirit and scope thereof.

What is claimed is:

1. A norbornane or norbornene compound of the formulae:

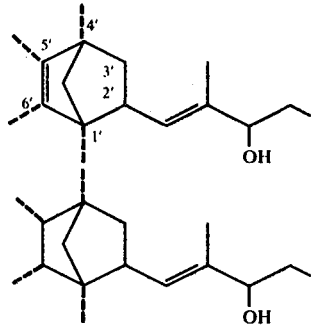

wherein one methyl group is present at one of the 1', 4', 5' or 6' positions of the nucleus of said compound.

2. The compound of claim 1 wherein said compound has the formula:

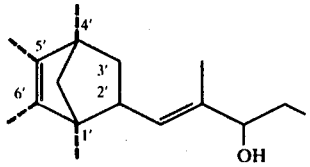

3. The compound of claim 1 wherein said compound has the formula:

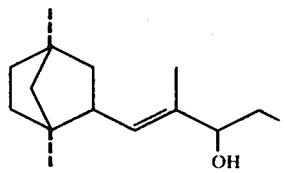

* * * * *